(12) United States Patent
Costanzo et al.

(10) Patent No.: US 6,495,523 B1
(45) Date of Patent: Dec. 17, 2002

(54) TRICYCLIC MONOSACCHARIDE DERIVATIVES USEFUL IN TREATING ACUTE ISCHEMIA-INDUCED NEURODEGENERATION

(75) Inventors: Michael J. Costanzo, Ivyland, PA (US); Bruce E. Maryanoff, New Hope, PA (US); Richard P. Shank, Blue Bell, PA (US)

(73) Assignee: Ortho McNeil-Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/620,510

(22) Filed: Jul. 20, 2000

Related U.S. Application Data

(60) Provisional application No. 60/145,618, filed on Jul. 26, 1999.

(51) Int. Cl.⁷ .......... A01N 61/00; A01N 43/04; A01N 57/36; A01N 57/00; A01N 43/26
(52) U.S. Cl. .......... 514/23; 514/1; 514/111; 514/118; 514/439; 514/455; 514/459; 514/463
(58) Field of Search .......... 514/439, 455, 514/459, 463, 1, 111, 118, 23

(56) References Cited

U.S. PATENT DOCUMENTS

| | | | |
|---|---|---|---|
| 5,242,942 A | 9/1993 | Costenzo et al. | 514/439 |
| 5,498,629 A | 3/1996 | Costenzo et al. | 514/439 |
| 6,323,236 B2 * | 11/2001 | McElroy | 514/439 |

FOREIGN PATENT DOCUMENTS

| | | |
|---|---|---|
| EP | 0568306 A | 11/1993 |
| EP | 0574256 A | 12/1993 |
| WO | 9517406 A | 6/1995 |
| WO | 9800124 A | 1/1998 |

OTHER PUBLICATIONS

B.E. Maryanoff et al: "Structure–Activity Studies on Anticonvulsant Sugar Sulfamates Related to Topiramate. Enhanced Potency with Cyclic Sulfate Derivatives." Journal of medicinal Chemistry., vol. 41, No. 8, 1998, pp. 1315–1343, XP002149867 American Chemical Society, Washington., US ISSN: 0022–2623.

* cited by examiner

Primary Examiner—Jezia Riley
(74) Attorney, Agent, or Firm—Ralph R. Palo

(57) ABSTRACT

Anticonvulsant compounds of the general formula I:

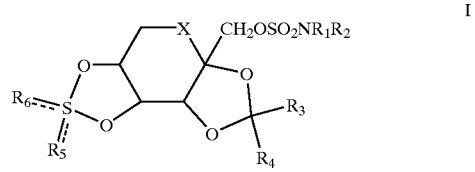

where $X$, $R_1$, $R_2$, $R_3$, $R_4$, $R_5$, and $R_6$ are as herein defined; are useful in treating acute ischemia-induced neurodegeneration, such as occurs during and after stroke, head trauma, spinal injury, non-fatal cardiac arrest, or major surgical procedures. Furthermore, pharmaceutical compositions containing a compound of formula I as well as methods for their use are disclosed.

25 Claims, No Drawings

TRICYCLIC MONOSACCHARIDE DERIVATIVES USEFUL IN TREATING ACUTE ISCHEMIA-INDUCED NEURODEGENERATION

This application calims benefit of Provisional Application No. 60/145,618, filed Jul. 26, 1999.

BACKGROUND OF THE INVENTION

Compounds of formula I:

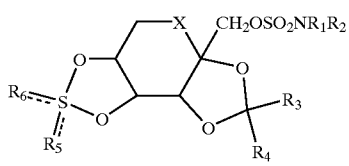

are structurally novel anticonvulsants (Maryanoff, B. E., Costanzo, M. J., Nortey, S. O., Greco, M. N., Shank, R. P., Schupsky, J. J., Ortegon, M. E., and Vaught, J. L. *J. Med. Chem.* 1998, 41, 1315–1343), found to possess anticonvulsant activity in the traditional maximal electroshock seizure (MES) test in mice and rats (Shank, R. P. et al., *Epilepsia* 1994, 35, 450–460). These compounds, covered by U.S. Pat. Nos. 5,242,942 and 5,498,629, are structurally related to 2,3:4,5-bis-O-(1-methylethylidene)-β-D-fructopyranose sulfamate, topiramate, which has been demonstrated in clinical trials of human epilepsy to be effective as adjunctive therapy or as monotherapy in treating simple and complex partial seizures and secondarily generalized seizures, and is currently marketed in the United States of America, as well as other countries worldwide.

Recent preclinical studies on compounds of formula I have revealed previously unrecognized pharmacological properties, suggesting that such compounds will be effective in treating certain other neurological disorders. One of these, in particular, is acute ischemia-induced neurodegeneration, such as that which occurs during and after stroke, head trauma, spinal injury, non-fatal cardiac arrest, or major surgical procedures.

SUMMARY OF THE INVENTION

Accordingly, it has been found that anticonvulsant compounds of the following formula I:

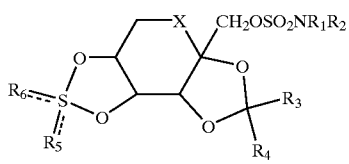

wherein X is oxygen or methylene, and $R_1$, $R_2$, $R_3$, $R_4$, $R_5$, and $R_6$ are as defined hereinafter, are useful in treating acute ischemia-induced neurodegeneration, such as occurs during and after head trauma, stroke, spinal injury, non-fatal cardiac arrest, or major surgical procedures.

DETAILED DESCRIPTION OF THE INVENTION

The sulfamates of the invention are of the following formula (I):

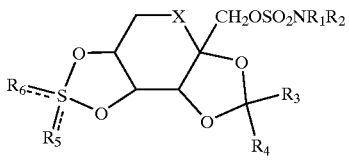

wherein

X is methylene or oxygen;

$R_1$ and $R_2$ are the same or different and chosen from hydrogen, $C_1$–$C_6$ alkyl, $C_3$–$C_6$ cycloalkyl, benzyl, allyl, or $C_1$–$C_6$ perfluoroalkylmethyl, or taken together as $N_2$ to define an azide group;

$R_3$ and $R_4$ are the same or different and chosen from hydrogen or $C_1$–$C_6$ alkyl;

$R_5$ and $R_6$ may be the same or different and are selected from oxygen, a lone pair of electrons or $NR_7$; wherein $R_7$ is selected from hydrogen, $C_1$–$C_6$ alkyl, $C_1$–$C_6$ perfluoroalkyl, arenesulfonyl, $C_1$–$C_6$ alkoxycarbonyl or arenemethyloxycarbonyl.

As used herein alkyl, alkoxy and perfluoroalkyl include straight and branched chains. For example, alkyl radicals include methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, n-hexyl, 1-methylpentyl, 3-methylpentyl and n-octyl. Perfluoroalkyl radicals are defined as the previously described straight or branched chain alkyl radicals in which all of the hydrogen atoms have been replaced with fluorine atoms, e.g. trifluoromethyl, pentafluoroethyl, heptafluoropropyl, etc. Alkoxy radicals are oxygen ethers formed from the previously described straight or branched chain alkyl groups. Arenesulfonyl radicals include, for example, phenylsulfonyl, o-toluenesulfonyl, m-toluenesulfonyl, p-toluenesulfonyl (abbreviated as "Ts"), 1-naphthalenesulfonyl, 2-naphthalenesulfonyl, and 5-dimethylamino-1-naphthalenesulfonyl.

The compounds of formula I include the various individual isomers as well as the racemates thereof, e.g., the various alpha and beta attachments, i.e., below and above the plane of the drawing, of $R_3$, $R_4$, $R_5$ and $R_6$ on the 6-membered ring. Preferably, the oxygens of the methylenedioxy group of formula I are attached on the same side of the 6-membered ring.

Cyclic sulfites are designated when either $R_5$ is oxygen and $R_6$ is a lone pair of electrons and vice versa. Cyclic sulfates are designated when $R_5$ and $R_6$ are both oxygen. Cyclic imidosulfites are designated $R_5$ is $NR_7$ and $R_6$ is a lone pair of electrons and vice versa. Cyclic imidosulfates are designated when $R_5$ is $NR_7$ and $R_6$ is oxygen and vice versa. Cyclic diimidosulfates are designated when $R_5$ and $R_6$ both equal $NR_7$.

The system of stereodescription developed by Cahn, Ingold and Prelog and described in *Angew. Chem. Int. Ed. Engl.* 1966, 5, 385 is used herein to describe the absolute stereochemistry of stereogenic sulfur atoms. For example, the structure of (R)-2,3-O-(1-methylethylidene)-4,5-O-sulfinyl-β-D-fructopyranose sulfamate is shown below:

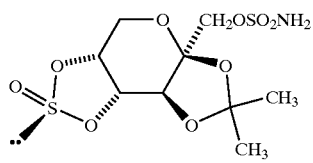

Compounds of formula (I) can exist in the β-D-fructopyranose and the β-L-fructopyranose absolute configurations. As used herein, the β-D-fructopyranose absolute configuration is defined as:

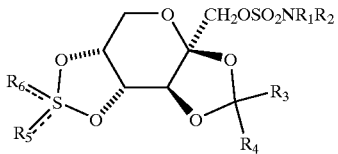

and the β-L-fructopyranose absolute configuration is defined as:

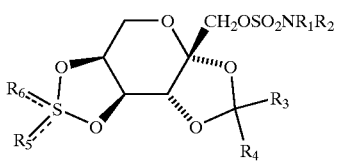

Compounds of formula (I) can also exist in the pseudo-β-D-fructopyranose and the β-L-fructopyranose absolute configurations. As used herein, the pseudo-β-D-fructopyranose absolute configuration is defined as:

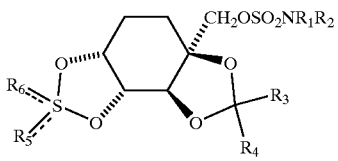

and the pseudo-β-L-fructopyranose absolute configuration is defined as:

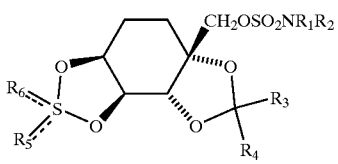

A particular group of compounds of formula I is that wherein X is oxygen or methylene; $R_1$ and $R_2$ are the same or different and selected from hydrogen, methyl, or ethyl, or different with one equal to hydrogen and the other selected from cyclopropyl or cyclobutyl; $R_3$ and $R_4$ are the same or different and selected from hydrogen, methyl, or ethyl; $R_5$ and $R_6$ are both oxygen, or one is oxygen and the other a lone pair of electrons.

Preferred compounds of formula (I) are those wherein the compounds are in the β-D-fructopyranose absolute configuration wherein X is oxygen or methylene; $R_1$ and $R_2$ are as defined above; $R_3$ and $R_4$ are methyl; $R_5$ and $R_6$ are oxygen.

Particularly preferred compounds of formula (I) are those in the β-D-fructopyranose absolute configuration wherein; X is oxygen; $R_1$ and $R_2$ are the same or different and selected from hydrogen, methyl, or ethyl, or different with one equal to hydrogen and the other selected from cyclopropyl or cyclobutyl; $R_3$ and $R_4$ are the same or different and selected from hydrogen, methyl, or ethyl; $R_5$ and $R_6$ are both oxygen, or one is oxygen and the other a lone pair of electrons.

In addition, the compounds of this invention also include any pharmaceutically acceptable salts, for example: alkali metal salts, such as sodium and potassium; ammonium salts; monoalkylammonium salts; dialkylammonium salts; trialkylammonium salts; tetraalkylammonium salts; and tromethamine salts. Hydrates and other solvates of the compound of the formula (I) are included within the scope of this invention.

Examples of specific compounds of formula (I) are:

2,3-O-(1-methylethylidene)-4,5-O-sulfonyl-β-D-fructopyranose sulfamate, i.e. where the compound is in the β-D-fructopyranose absolute configuration, X is oxygen, $R_1$ and $R_2$ are hydrogen, $R_3$ and $R_4$ are methyl, $R_5$ and $R_6$ are oxygen;

2,3-O-(1-methylethylidene)-4,5-O-sulfonyl-β-L-fructopyranose sulfamate, i.e. where the compound is in the β-L-fructopyranose absolute configuration, X is oxygen, $R_1$ and $R_2$ are hydrogen, $R_3$ and $R_4$ are methyl, $R_5$ and $R_6$ are oxygen;

2,3-O-(1-methylethylidene)-4,5-O-sulfonyl-β-D-fructopyranose methylsulfamate, i.e. where the compound is in the β-D-fructopyranose absolute configuration, X is oxygen, $R_1$ is hydrogen, $R_2$ is methyl, $R_3$ and $R_4$ are methyl, $R_5$ and $R_6$ are oxygen;

2,3-O-(1-methylethylidene)-4,5-O-sulfonyl-β-D-fructopyranose butylsulfamate, i.e. where the compound is in the β-D-fructopyranose absolute configuration, X is oxygen, $R_1$ is hydrogen, $R_2$ is n-butyl, $R_3$ and $R_4$ are methyl, $R_5$ and $R_6$ are oxygen;

2,3-O-(1-methylethylidene)-4,5-O-sulfonyl-β-D-fructopyranose ethylsulfamate, i.e. where the compound is in the β-D-fructopyranose absolute configuration, X is oxygen, $R_1$ is hydrogen, $R_2$ is ethyl, $R_3$ and $R_4$ are methyl, $R_5$ and $R_6$ are oxygen;

2,3-O-(1-methylethylidene)-4,5-O-sulfonyl-β-D-fructopyranose octylsulfamate, i.e. where the compound is in the β-D-fructopyranose absolute configuration, X is oxygen, $R_1$ is hydrogen, $R_2$ is n-octyl, $R_3$ and $R_4$ are methyl, $R_5$ and $R_6$ are oxygen;

2,3-O-(1-methylethylidene)-4,5-O-sulfonyl-β-D-fructopyranose 2-propenylsulfamate, i.e. where the compound is in the β-D-fructopyranose absolute configuration, X is oxygen, $R_1$ is hydrogen, $R_2$ is allyl, $R_3$ and $R_4$ are methyl, $R_5$ and $R_6$ are oxygen;

2,3-O-(1-methylethylidene)-4,5-O-sulfonyl-β-D-fructopyranose phenylmethylsulfamate; i.e. where the compound is in the β-D-fructopyranose absolute configuration, X is oxygen, $R_1$ is hydrogen, $R_2$ is benzyl, $R_3$ and $R_4$ are methyl, $R_5$ and $R_6$ are oxygen;

2,3-O-(1-methylethylidene)-4,5-O-sulfonyl-β-D-fructopyranose cyclopropylsulfamate, i.e. where the compound is in the β-D-fructopyranose absolute configuration, X is oxygen, $R_1$ is hydrogen, $R_2$ is cyclopropyl, $R_3$ and $R_4$ are methyl, $R_5$ and $R_6$ are oxygen;

2,3-O-(1-methylethylidene)-4,5-O-sulfonyl-β-D-fructopyranose cyclobutylsulfamate, i.e. where the compound is in the β-D-fructopyranose absolute configuration, X is oxygen, $R_1$ is hydrogen, $R_2$ is cyclobutyl, $R_3$ and $R_4$ are methyl, $R_5$ and $R_6$ are oxygen;

2,3-O-(1-methylethylidene)-4,5-O-sulfonyl-β-D-fructopyranose cyclooctylsulfamate, i.e. where the compound is in the β-D-fructopyranose absolute configuration, X is oxygen, $R_1$ is hydrogen, $R_2$ is cyclooctyl, $R_3$ and $R_4$ are methyl, $R_5$ and $R_6$ are oxygen;

2,3-O-(1-methylethylidene)-4,5-O-sulfonyl-β-D-fructopyranose (2,2,2-trifluoroethyl)-sulfamate, i.e. where the compound is in the β-D-fructopyranose absolute configuration, X is oxygen, $R_1$ is hydrogen, $R_2$ is 2,2,2-trifluoroethyl, $R_3$ and $R_4$ are methyl, $R_5$ and $R_6$ are oxygen;

2,3-O-(1-methylethylidene)-4,5-O-sulfonyl-β-D-fructopyranose dimethylsulfamate, i.e. where the compound is in the β-D-fructopyranose absolute configuration, X is oxygen, $R_1$ and $R_2$ are methyl, $R_3$ and $R_4$ are methyl, $R_5$ and $R_6$ are oxygen;

2,3-O-(1-methylethylidene)-4,5-O-sulfonyl-β-D-fructopyranose diethylsulfamate, i.e. where the compound is in the β-D-fructopyranose absolute configuration, X is oxygen, $R_1$ and $R_2$ are ethyl, $R_3$ and $R_4$ are methyl, $R_5$ and $R_6$ are oxygen;

2,3-O-(1-methylethylidene)-4,5-O-sulfonyl-β-D-fructopyranose azidosulfate, i.e. where the compound is in the β-D-fructopyranose absolute configuration, X is oxygen, $R_1$ and $R_2$ are taken together with the nitrogen of formula (I) to represent an azido ($N_3$) group, $R_3$ and $R_4$ are methyl, $R_5$ and $R_6$ are oxygen;

(S)-2,3-O-(1-methylethylidene)-4,5-O-sulfinyl-β-D-fructopyranose sulfamate, i.e. where the compound is in the β-D-fructopyranose absolute configuration, X is oxygen, $R_1$ and $R_2$ are hydrogen, $R_3$ and $R_4$ are methyl, $R_5$ is oxygen, $R_6$ is a lone pair of electrons, and the absolute stereochemistry at the sulfite sulfur is (S);

(R)-2,3-O-(1-methylethylidene)-4,5-O-sulfinyl-β-D-fructopyranose sulfamate, i.e. where the compound is in the β-D-fructopyranose absolute configuration, X is oxygen, $R_1$ and $R_2$ are hydrogen, $R_3$ and $R_4$ are methyl, $R_5$ is a lone pair of electrons, $R_6$ is oxygen, and the absolute stereochemistry at the sulfite sulfur is (R);

2,3-O-(1-ethylpropylidene)-4,5-O-sulfonyl-β-D-fructopyranose sulfamate, i.e. where the compound is in the β-D-fructopyranose absolute configuration, X is oxygen, $R_1$ and $R_2$ are hydrogen, $R_3$ and $R_4$ are ethyl, $R_5$ and $R_6$ are oxygen;

2,3-O-(1-methylethylidene)-4,5-O-[N-(4-methylbenzenesulfonyl) imidosulfinyl]-β-D-fructopyranose sulfamate, i.e. where the compound is in the β-D-fructopyranose absolute configuration, X is oxygen, $R_1$ and $R_2$ are hydrogen, $R_3$ and $R_4$ are methyl, $R_5$ is $NR_7$, $R_6$ is a lone pair of electrons, and $R_7$ is p-toluenesulfonyl;

2,3-O-(1-methylethylidene)-4,5-O-[N-(4-methylbenzenesulfonyl) imidosulfonyl]-β-D-fructopyranose sulfamate, i.e. where the compound is in the β-D-fructopyranose absolute configuration, X is oxygen, $R_1$ and $R_2$ are hydrogen, $R_3$ and $R_4$ are methyl, $R_5$ is $NR_7$, $R_6$ is oxygen, and $R_7$ is p-toluenesulfonyl;

2,3-O-(cyclohexylidene)-4,5-O-sulfonyl-β-D-fructopyranose sulfamate, i.e. where the compound is in the β-D-fructopyranose absolute configuration, X is oxygen, $R_1$ and $R_2$ are hydrogen, $R_3$ and $R_4$ are taken together with carbon to which they are both bonded to represent a cyclohexane ring, $R_5$ and $R_6$ are oxygen;

(R)-4,5-O-[N-(1,1-dimethylethoxycarbonyl)imidosulfinyl]-2,3-O-(1-methylethylidene)-β-D-fructopyranose sulfamate, i.e. where the compound is in the β-D-fructopyranose absolute configuration, X is oxygen, $R_1$ and $R_2$ are hydrogen, $R_3$ and $R_4$ are methyl, $R_5$ is a lone pair of electrons, $R_6$ is $NR_7$, $R_7$ is t-butoxycarbonyl, and the absolute stereochemistry at the imidosulfite sulfur is (R);

(S)-4,5-O-[N-(1,1-dimethylethoxycarbonyl)imidosulfinyl]-2,3-O-(1-methylethylidene)-β-D-fructopyranose sulfamate, i.e. where the compound is in the β-D-fructopyranose absolute configuration, X is oxygen, $R_1$ and $R_2$ are hydrogen, $R_3$ and $R_4$ are methyl, $R_5$ is $NR_7$, $R_6$ is a lone pair of electrons, $R_7$ is t-butoxycarbonyl, and the absolute stereochemistry at the imidosulfite sulfur is (S);

2,3-O-(1-methylethylidene)-4,5-O-sulfonyl-pseudo-β-D-fructopyranose sulfamate, i.e. where the compound is in the β-D-fructopyranose absolute configuration, X is methylene, $R_1$ and $R_2$ are hydrogen, $R_3$ and $R_4$ are methyl, $R_5$ and $R_6$ are oxygen;

2,3-O-(1-methylethylidene)-4,5-O-sulfonyl-pseudo-β-L-fructopyranose sulfamate, i.e. where the compound is in the β-L-fructopyranose absolute configuration, X is methylene, $R_1$ and $R_2$ are hydrogen, $R_3$ and $R_4$ are methyl, $R_5$ and $R_6$ are oxygen;

2,3-O-(1-methylethylidene)-4,5-O-sulfonyl-pseudo-β-D-fructopyranose methylsulfamate, i.e. where the compound is in the β-D-fructopyranose absolute configuration, X is methylene, $R_1$ is hydrogen, $R_2$ is methyl, $R_3$ and $R_4$ are methyl, $R_5$ and $R_6$ are oxygen;

2,3-O-(1-methylethylidene)-4,5-O-sulfonyl-pseudo-β-D-fructopyranose cyclopropyl-sulfamate, i.e. where the compound is in the β-D-fructopyranose absolute configuration, X is methylene, $R_1$ is hydrogen, $R_2$ is cyclopropyl, $R_3$ and $R_4$ are methyl, $R_5$ and $R_6$ are oxygen;

2,3-O-(1-methylethylidene)-4,5-O-sulfonyl-pseudo-β-D-fructopyranose cyclobutyl-sulfamate, i.e. where the compound is in the β-D-fructopyranose absolute configuration, X is methylene, $R_1$ is hydrogen, $R_2$ is cyclobutyl, $R_3$ and $R_4$ are methyl, $R_5$ and $R_6$ are oxygen;

(S)-2,3-O-(1-methylethylidene)-4,5-O-sulfinyl-pseudo-β-D-fructopyranose sulfamate, i.e. where the compound is in the β-D-fructopyranose absolute configuration, X is methylene, $R_1$ and $R_2$ are hydrogen, $R_3$ and $R_4$ are methyl, $R_5$ is oxygen, $R_6$ is a lone pair of electrons, and the absolute stereochemistry at the sulfite sulfur is (S);

(R)-2,3-O-(1-methylethylidene)-4,5-O-sulfinyl-pseudo-β-D-fructopyranose sulfamate, i.e. where the compound is in the β-D-fructopyranose absolute configuration, X is methylene, $R_1$ and $R_2$ are hydrogen, $R_3$ and $R_4$ are methyl, $R_5$ is a lone pair of electrons, $R_6$ is oxygen, and the absolute stereochemistry at the sulfite sulfur is (R);

and the pharmaceutically acceptable salts thereof.

The compounds of formula I can be made by one skilled in the art of synthetic organic chemistry by the processes disclosed in U.S. Pat. Nos. 4,513,006, 5,242,942, and 5,498,629, which are incorporated by reference herein. These procedures are also described in greater detail in Maryanoff, B. E., Costanzo, M. J., Nortey, S. O., Greco, M. N., Shank, R. P., Schupsky, J. J., Ortegon, M. E., and Vaught, J. L. *J. Med. Chem.* 1998, 41, 1315–1334) and McComsey, D. F., Maryanoff, B. E .*J. Org. Chem.* 1994, 59, 2652–2654. Some example syntheses that are described in these references are as follows:

(a) Reaction of an alcohol of the formula $RCH_2OH$ with a chlorosulfamate of the formula $ClSO_2NH_2$ or $ClSO_2NHR_1$ in the presence of a base such as potassium tert-butoxide or sodium hydride at a temperature of about −20° to 25° C. and in a solvent such as toluene, THF or dimethylformamide wherein R is a moiety of formula II, wherein X, $R_3$, $R_4$, $R_5$, and $R_6$ are as previously defined.

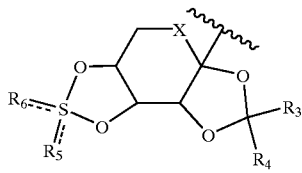

(b) Reaction of an alcohol of the formula $RCH_2OH$ with sulfuryl chloride in the presence of a base such as triethylamine or pyridine at a temperature of about $-40°$ to $25°$ C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1R_2NH$ at a temperature of about $40°$ to $25°$ C. in a solvent such as methylene chloride or acetonitrile to produce a compound of formula I. The reaction conditions for (b) are also described by T. Tsuchiya et al. in *Tetrahedron Lett* 1978, 36, 3365–3368.

(c) Reaction of the chlorosulfate $RCH_2OSO_2Cl$ with a metal azide such as sodium azide in a solvent such as methylene chloride or acetonitrile yields an azidosulfate of the formula $RCH_2OSO_2N_3$ as described by M. Hedayatullah in *Tetrahedron Lett.* 1975, 2455–2458. The azidosulfate is then reduced to a compound of formula (I) wherein $R_1$ is hydrogen by catalytic hydrogenation, e.g. with a noble metal and $H_2$ or by heating with copper metal in a solvent such as methanol.

For treating acute ischemia-induced neurodegeneration caused by stroke, head trauma, spinal injury, non-fatal cardiac arrest, or any major surgical procedure a compound of formula I may be employed by administering a single iv dosage in the range of about 25 to 1600 mg within a period of several hours after the medical condition is identified, for an average adult human.

Biological Studies

Male Long-Evans rats (250 g) were obtained from Charles River Laboratories, Portage, Mich. The neurologic function and seizure susceptibility of each animal was tested according to the methods described below. The rats were housed in the experimental laboratory for at least 24 h prior to study to avoid transit stress and to ensure a 24-h fasting period. Only rats with blood glucose levels of 100 mg/dL or less at the end of fasting were used in the experiments.

General anesthesia was induced with ketamine (100 mg/kg, ip) and maintained with small fractional supplements as needed. Tracheal intubation was performed using a custom-made fiberoptic rodent laryngoscope and a 14-gauge polyethylene catheter. Needle electrodes were inserted in the scalp and thorax to monitor the EEG and ECG, respectively, while blood pressure was measured via an indwelling femoral arterial cannula. Body and brain temperatures were monitored by thermistors placed in the rectum and temporalis muscle, respectively. Once the temporalis temperature was stabilized at 34.5±0.5° C. the ischemic insult was produced by hydraulic atraumatic chest compression (3-kg force) for 11.0 min. Cranial temperature was maintained during circulatory arrest with the aid of a heat lamp. Chest compression resulted in complete global ischemia due to cardiac electromechanical dissociation. The completeness of the ischemic insult was verified by the absence of an arterial pressure waveform and EEG electrical activities. After the period of compression, resuscitation was initiated by external cardiac massage and mechanically assisted ventilation with 95% oxygen. Rats in which spontaneous ECG activity did not return within 5 min were immediately sacrificed. Assisted ventilation was continued until persistent spontaneous ventilation occurred. Rats requiring assisted ventilation for more than 1 h were sacrificed. After spontaneous respiration was restored, the inspired oxygen concentration was reduced to 50% and the rats were extubated 30 min later.

Neurologic assessment was identical to that described for the use with this model by Wauquier et al. (*Neuropharmacology* 1989; 28(8):837–846). Assessments were made on the fifth day following the insult by a single experienced observer who was blinded to the nature of the experimental variable. The assessment provided a 50-point clinical scoring system (0=normal, i.e., no deficit) that characterized decrements in cranial and spinal reflexes, postural tone, placing reactions, gait and spontaneous locomotor behavior. In addition to the neurodeficit score, the angle of inclination at which the rat could no longer cling to the inclined plane was determined. Performance was quantified as percent of preinsult baseline.

Audiogenic convulsions were induced in previously insulted rats by vigorously shaking a small ring of common house keys at a distance of 0.5 m for a period of 1 min. Keys were used because they were much more effective than high intensity (90 dB) pure tone (10 to 20 kHz) stimuli used in preliminary observations. In their simplest form, the audiogenic convulsions were characterized by wild running, with increasing severity, convulsions progressed to clonus and ultimately whole body tonic extension. The postictal period was characterized by profound behavioral depression. The 9-point scale, originally developed by Dailey & Jobe (*Fed Proc.* 1985; 44: 2640–2644) for scoring audiogenic convulsions in genetically epilepsy-prone rats, was used to measure seizure severity. On this scale, 0 was normal and 9 was the most severe form of convulsion.

Postischemic injury (pyknosis, crenation) in hippocampal CA1 pyramidal neurons was quantified on the fifth recovery day. Rats were sacrificed by an overdose of pentobarbital and the brains were perfusion-fixed with 10% buffered formalin. Slides containing successive 10-micron sections of the CA1 hippocampal region (3000 μm posterior to bregma) were stained with cresyl violet. A pair of representative slides containing dorsal hippocampus was obtained from each animal. Photographs of a medium power field were used to count ischemic (darkly stained) pyramidal neurons. Ischemic cell counts were expressed as a percent of the total number of CA1 neurons per photograph.

In addition to these subjective assessments of reperfusion injury, objective electrophysiologic measures were performed on 6 rats to more clearly document the character of the ischemic damage. During brainstem auditory evoked potential (BSAEP) analysis, the acoustic stimuli were rarefaction clicks delivered at 2 Hz and an intensity of 80 dB through miniature ear pieces. Two thousand responses were averaged, using a Cadwell 7400 signal analyzer. The latency from the stimulus artifact to the fourth positive component (wave IV) was used as a measure of brainstem excitability.

Conditions for the production of middle latency auditory evoked potentials (MLAEP) were the same. Since the middle latency components of the auditory evoked potentials are thought to arise from the thalamocortical radiations, a latency increase in the stable P1wave was used as a measure of depressed cortical auditory function. Recordings of both types of auditory evoked potentials were made from animals anesthetized with ketamine 100 mg/kg ip.

Somatosensory evoked potential (SSEP) and EEG recordings were made from awake unmedicated animals that were gently restrained with a soft cloth towel. During SSEP analysis, the posterior tibial nerve was stimulated with needle electrodes using a 100 μsec pulse of 20 mA and 250 repetitions. Latency increase of the early stable P1 component indicated delayed transmission through spinal cord/brain stem sensory pathways.

A Probit analysis of the dose-response relationships was performed to establish $ED_{50}$ values and the 95% confidence limits.

Under the experimental conditions described for this study, RWJ-37947 significantly reduced the ischemia-induced neurological deficit and the detrimental effect on exploratory behavior (Table 1).

TABLE 1

NEUROPROTECTIVE EFFICACY OF RWJ-37947 IN A RAT CARDIAC ARREST MODEL

|  | Neural Impairment Improvement Vs Paired Controls* |
| --- | --- |
| Seizure Incidence | NS |
| Seizure severity | NS |
| Neurological deficit | 0.0001 |
| Inclined plane (grip strength) | NS |
| Exploratory behavior | 0.001 |

*P values are less than the number specified.
NS indicates not statistically significant (P > 0.05)
RWJ-37947 was administered iv (20 mg/kg) 30 min post-resuscitation and po (20 mg/kg) 2 hr post-resuscitation. (N = 6 rats).

The compounds of formula I preferably are administered in the form of a pharmaceutical composition. To prepare the pharmaceutical compositions of this invention, one or more sulfamate compounds of formula I are intimately admixed with a pharmaceutical carrier according to conventional pharmaceutical compounding techniques, which carrier may take a wide variety of forms depending on the form of preparation desired for administration, e.g., oral, subcutaneous, parenteral or by suppository. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral unit dosage form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for purposes such as aiding solubility or for preservation, may be included. Injectable suspensions may also be prepared, in which case appropriate liquid carriers, suspending agents and the like may be employed.

It is especially advantageous to formulate the aforementioned pharmaceutical compositions in unit dosage form for ease of administration and uniformity of dosage. The term "unit dosage form" as used in the specification and claims herein refers to physically discrete units suitable as unit dosages, each unit containing a predetermined quantity of active ingredient calculated to produce the desired therapeutic effect in association with the required pharmaceutical carrier.

The pharmaceutical compositions herein will contain, per unit dosage, e.g., tablet, capsule, powder, injection, teaspoonful, suppository and the like. The compositions will be administrated in amounts as previously described herein with regard to the active ingredient and to the condition being treated. The dosages, however, may be varied depending upon the requirement of the patient, the severity of the condition being treated, and the compound being employed. Determination of optimum dosages for a particular situation is within the skill of the art.

In the following Examples and throughout the specification the following terms and abbreviations are used: g (grams); mL (milliliters); L (liters); min (minutes); hr (hours); mol (moles); v/v (volume to volume); DMF (N,N-dimethylformamide); $Et_2O$ (diethyl ethyl); EtOAc (ethyl acetate); NBS (N-bromosuccinimide); THF (tetrahydrofuran); RT (room temperature); C, H, N, etc. (the chemical symbols for the elements); Calcd. (calculated); $[\alpha]_D^{25}$ (specific rotation measured at 25° C. with 589 nanometer light); c (concentration in grams per 100 mL); mp (melting point); decomp. (decomposition); TLC (thin layer chromatography); and Celite® (filter agent). All melting points are corrected.

EXAMPLE 1

2,3-O-(1-Methylethylidene)-4,5-O-sulfonyl-β-D-fructopyranose Sulfamate

A 3 L three-necked flask was equipped with a mechanical stirrer, thermometer, addition funnel, and an argon inlet. 2,3-O-(1-Methylethylidene)-β-D-fructopyranose 1-sulfamate (50.0 g, 0.167 mol) was combined with EtOAc (1.7 L) and pyridine (31.7 g, 0.401 mol). This mixture was heated at reflux while stirring under argon to effect solution and cooled to −60° C. with a dry ice/isopropanol bath. Sulfuryl chloride (49.6 g, 0.370 mol) was added dropwise over 45 min at −60 to −50° C. while stirring under argon. The resulting white slurry was stirred at −60 to −50° C. for 1 hr, then at RT for 2 hr, and filtered through Celite®. The filtrate was extracted sequentially with saturated aqueous NaCl, 1N HCl, saturated aqueous $NaHCO_3$ (twice), saturated aqueous NaCl, dried over anhydrous $MgSO_4$, filtered through Celite® and concentrated in vacuo at 40° C. to furnish 85.6 g (100%) of 4,5-bis-O-chlorosulfonyl-2,3-O-(1-methylethylidene)-β-D-fructopyranose sulfamate as a white crystalline solid, which was used without further purification. An analytical sample was purified by column chromatography on silica gel eluting with $CH_2Cl_2$/EtOAc (95:5 v/v); mp 119–121° C. (decomp.).

A solution of 4,5-bis-O-chlorosulfonyl-2,3-O-(1-methylethylidene)-β-D-fructopyranose sulfamate (83.1 g, 0.167 mol) in 418 mL of methanol was combined with $NaHCO_3$ (84.2 g, 1.00 mol) at RT in a 2 L three-necked flask equipped with a mechanical stirrer and an argon inlet. This mixture was stirred at RT under argon for 18 hr, filtered through Celite® and concentrated in vacuo at 40° C. The residue was dissolved in EtOAc and extracted twice with saturated aqueous NaCl, dried over anhydrous $MgSO_4$, filtered through Celite® and concentrated in vacuo at 40° C.

to afford 59.3 g (98%) of product as an oil which crystallized on standing. This material was purified by column chromatography on silica gel eluting with $CH_2Cl_2$/EtOAc (9:1 v/v) to furnish 36.6 g (53%) of product. The isolated product (36.6 g) was dissolved in anhydrous ethanol (total volume =150 mL), filtered through Celite®, diluted to 350 mL with water, seeded and allowed to recrystallize at 5° C. The resulting white crystals were washed with a cold mixture of ethanol/water (1:1), then with water and dried in vacuo at 40° C. (18 h) to give 31.4 g of pure 2,3-O-(1-methylethylidene)-O-4,5-sulfonyl-β-D-fructopyranose sulfamate, mp 139–141° C. (decomp.); $[\alpha]_D^{25}$=–28.8° (c=1.17, $CH_3OH$). Anal. Calcd. for $C_9H_{15}NO_{10}S_2$: C, 29.92; H, 4.18; N, 3.88. Found: C, 30.01; H, 4.36; N, 3.80.

EXAMPLE 2

2,3-O-(1-Methylethylidene)-4,5-O-sulfonyl-β-L-fructopyranose Sulfamate 2,3-O-(1-Methylethylidene)-β-L-fructopyranose 1-sulfamate was prepared from L-fructose using the same procedure described for the D-isomer (*J. Med. Chem.* 1987, 30, 880) mp=124–127° C. (decomp.); $[\alpha]_D^{25}$=–26.4° (c=0.83, $CH_3OH$). The 2,3-O-(1-methylethylidene)-β-L-fructopyranose 1-sulfamate thus obtained was converted to the title compound using the procedure described above for Example 1 (i.e. the D-isomer) to provide 1.19 g of 2,3-O-(1-methylethylidene)-4,5-O-sulfonyl-β-L-fructopyranose sulfamate, mp 128–129° C. (decomp.); $[\alpha]_D^{25}$=+27.10 (c=1.18, $CH_3OH$). Anal. Calcd. for $C_9H_{15}NO_{10}S_2$: C, 29.92; H, 4.18; N, 3.88; S, 17.75. Found: C, 30.07; H, 4.18; N, 3.83; S, 17.62.

EXAMPLE 3

2,3-O-(1-Methylethylidene)-4,5-O-sulfonyl-β-D-fructopyranose Methylsulfamate

A 1 L three-necked flask containing a solution of sulfuryl chloride (17.1 g, 0.127 mol) in 100 mL of dry toluene was equipped with a mechanical stirrer, thermometer, addition funnel, and an argon inlet and cooled to –60° C. A solution of 2,3-O-(1-methylethylidene)-4,5-O-sulfonyl-β-D-fructopyranose (29.8 g, 0.101 mol; *Can. J. Chem.* 1982, 60, 1857) and pyridine (10.0 g, 0.127 mol) in 422 mL of toluene was added dropwise to the sulfuryl chloride solution over 45 min at –5 to –60 ° C. while stirring vigorously under argon. After 2 hr at –55 to –60° C., the reaction was filtered through a pad of Celite®. The filtrate was extracted sequentially with water, twice with 1N $H_2SO_4$, twice with saturated aqueous $NaHCO_3$, twice with saturated aqueous NaCl, dried over anhydrous $MgSO_4$, filtered through a pad of Celite® and concentrated in vacuo to afford 31.9 g of crude chlorosulfate as a brown oil. This material was purified by column chromatography on silica gel eluting with $CH_2Cl_2$ to provide 28.9 g (72%) of 2,3-O-(1-methylethylidene)-4,5-O-sulfonyl-β-D-fructopyranose chlorosulfate as a white crystalline solid. An analytical sample was recrystallized from anhydrous ethanol; mp 93–95° C.; $[\alpha]_D^{25}$=–35.4° (c=0.86, $CH_3OH$). Anal. Calcd. for $C_9H_{13}ClO_{10}S_2$: C, 28.39; H, 3.44; Cl, 9.31; S, 16.84. Found: C, 28.53; H, 3.46; Cl, 9.17; S, 16.98.

The 2,3-O-(1-methylethylidene)-4,5-O-sulfonyl-β-D-fructopyranose chlorosulfate thus obtained (2.48 g, 0.0065 mol) was dissolved in 33 mL of THF and cooled to 5° C. while stirring under argon. Excess anhydrous methylamine was bubbled through the solution over 30 min while maintaining the temperature between 5 and 10° C. After 30 min, the reaction was filtered through a pad of Celite® concentrated in vacuo and the residue was chromatographed on silica gel eluting with hexane/EtOAc (85:15 v/v) to furnish 2.21 g (90%) of 2,3-O-(1-methylethylidene)-4,5-O-sulfonyl-β-D-fructopyranose methylsulfamate as clear hard glass; $[\alpha]_D^{25}$=–25.3 (c=1.00, $CH_3OH$). Anal. Calcd. for $C_{10}H_{17}NO_{10}S_2$: C, 32.00; H, 4.56; N, 3.73. Found: C, 32.30; H, 4.54; N, 3.83.

EXAMPLE 4

2,3-O-(1-Methylethylidene)-4,5-O-sulfonyl-β-D-fructopyranose Butylsulfamate 2,3-O-(1-Methylethylidene)-4,5-O-sulfonyl-β-D-fructopyranose chlorosulfate (2.49 g, 0.0065 mol), prepared as described in Example 3, was dissolved in 33 mL of THF, cooled to 5 C via an ice bath and treated with anhydrous n-butylamine (5.77 g, 0.079 mol) while stirring under argon. Fifteen minutes after the addition, the ice bath was removed and the reaction was stirred at RT for 4 hr, concentrated in vacuo, and purified by column chromatography on silica gel eluting with hexane/EtOAc (7:3 v/v) and recrystallized from ethanol/water (3:1 v/v) to provide 2.01 g (74%) of 2,3-O-(1-methylethylidene)-4,5-O-sulfonyl-β-D-fructopyranose butylsulfamate as a white crystalline solid; mp 111–113° C.; $[\alpha]_D^{25}$=–25.1° (c=1.00, $CH_3OH$). Anal. Calcd. for $C_{13}H_{23}NO_{10}S_2$: C, 37.40; H, 5.55; N, 3.36 Found: C, 37.87; H, 5.65; N, 3.30.

EXAMPLE 5

2,3-O-(1-Methylethylidene)-4,5-O-sulfonyl-β-D-fructopyranose Ethylsulfamate

Excess anhydrous ethylamine was reacted with 2,3-O-(1-methylethylidene)-4,5-O-sulfonyl-β-D-fructopyranose chlorosulfate (2.54 g, 0.0066 mol) in the same manner as described in Example 3 and chromatographed on silica gel eluting with hexane/EtOAc (4:1 v/v) to provide 2.30 g (89%) of 2,3-O-(1-methylethylidene)-4,5-O-sulfonyl-β-D-fructopyranose ethylsulfamate as a hard glass; $[\alpha]_D^{25}$=–23.6° (c=1.00, $CH_3OH$). Anal. Calcd. for $C_{11}H_{19}NO_{10}S_2 \cdot 0.2$ EtOAc: C, 34.82; H, 5.10; N, 3.44. Found: C, 35.04; H, 4.84; N, 3.13.

EXAMPLE 6

2,3-O-(1-Methylethylidene)-4,5-O-sulfonyl-β-D-fructopyranose Octylsulfamate

Excess anhydrous octylamine (2.46 mL, 0.0148 mol) was reacted with 2,3-O-(1-methylethylidene)-4,5-O-sulfonyl-β-D-fructopyranose chlorosulfate (1.88 g, 0.0049 mol) in the same manner as described in Example 4 and chromatographed on silica gel eluting with $CH_2Cl_2$/EtOAc (4:1 v/v) to provide 1.11 g (48%) of 2,3-O-(1-methylethylidene)-4,5-O-sulfonyl-β-D-fructopyranose octylsulfamate as an oil; $[\alpha]_D^{25}$=–17.1° (c=1.00, $CH_3OH$). Anal. Calcd. for $C_{17}H_{31}NO_{10}S_2 \cdot 0.1$ EtOAc: C, 43.33; H, 6.64; N, 2.90; S, 13.29 Found: C, 43.64; H, 6.68; N, 3.02; S, 13.06.

EXAMPLE 7

2,3-O-(1-Methylethylidene)-4,5-O-sulfonyl-β-D-fructopyranose 2-Propenylsulfamate Excess anhydrous allylamine (1.35 g, 0.0236 mol) was reacted with 2,3-O-1-methylethylidene)-4,5-O-sulfonyl-β-

D-fructopyranose chlorosulfate (3.00 g, 0.0079 mol) in the same manner as described in Example 4, filtered through a pad of Celite®, concentrated in vacuo, and dissolved in EtOAc. The EtOAc solution was extracted twice with 1N HCl, saturated aqueous NaHCO$_3$, and saturated aqueous NaCl and then dried over anhydrous MgSO$_4$. The EtOAc was removed in vacuo and the residue was purified by column chromatography on silica gel eluting with hexane/EtOAc (7:3 v/v) and recrystallized from ethanol/water (1:1 v/v) to provide 1.75 g (55%) of 2,3-O-(1-methylethylidene)-4,5-O-sulfonyl-β-D-fructopyranose 2-propenylsulfamate as a white crystalline solid; mp 75–77° C.; $[\alpha]_D^{25}=-31.1°$ (c=1.00, CH$_3$OH). Anal. Calcd. for C$_{12}$H$_{19}$NO$_{10}$S$_2$: C, 35.91 H, 4.77; N, 3.49; S, 15.97 Found: C, 35.98; H, 4.75; N, 3.49; S, 16.05.

EXAMPLE 8

2,3-O-(1-Methylethylidene)-4,5-O-sulfonyl-β-D-fructopyranose Phenylmethylsulfamate Excess anhydrous benzylamine (1.69 g, 0.0158 mol) was reacted with 2,3-O-(1-methylethylidene)-4,5-O-sulfonyl-β-D-fructopyranose chlorosulfate (2.00 g, 0.0053 mol) in the same manner as described in Example 4 and purified by column chromatography on silica gel eluting with hexane/EtOAc (7:3 v/v) to provide 1.73 g (72%) of 2,3-O-(1-methylethylidene)-4,5-O-sulfonyl-β-D-fructopyranose phenylmethylsulfamate as a white foam; $[\alpha]_D^{25}=-22.8°$ (c=1.00, CH$_3$OH). Anal. Calcd. for C$_{16}$H$_{21}$NO$_{10}$S$_2$: C, 42.57; H, 4.69; N, 3.10; S, 14.20. Found: C, 42.77; H, 4.68; N, 3.15; S, 14.26.

EXAMPLE 9

2,3-O-(1-Methylethylidene)-4,5-O-sulfonyl-β-D-fructopyranose Cyclopropylsulfamate Excess anhydrous cyclopropylamine (0.90 g, 0.0172 mol) was reacted with 2,3-O-(1-methylethylidene)-4,5-O-sulfonyl-β-D-fructopyranose chlorosulfate (2.00 g, 0.0053 mol) in the same manner as described in Example 4 to give 0.95 g (45%) of 2,3-O-(1-methylethylidene)-4,5-O-sulfonyl-β-D-fructopyranose cyclopropylsulfamate as a white foam after chromatography on silica gel eluting with hexane/EtOAc (4:1 v/v); $[\alpha]_D^{25}=-24.8°$ (c=1.00, CH$_3$OH). Anal. Calcd. for C$_{12}$H$_{19}$NO$_{10}$S$_2$: C, 35.91 H, 4.77; N, 3.49; S, 15.97 Found: C, 36.16; H, 4.83; N, 3.43; S, 15.81.

EXAMPLE 10

2,3-O-(1-Methylethylidene)-4,5-O-sulfonyl-β-D-fructopyranose Cyclobutylsulfamate Excess anhydrous cyclobutylamine (1.12 g, 0.0158 mol) was reacted with 2,3-O-(1-methylethylidene)-4,5-O-sulfonyl-β-D-fructopyranose chlorosulfate (2.00 g, 0.0053 mol) in the same manner as described in Example 4 to give 1.89 g (87%) of 2,3-O-(1-methylethylidene)-4,5-O-sulfonyl-β-D-fructopyranose cyclobutylsulfamate as a white foam after chromatography on silica gel eluting with hexane/EtOAc (4:1 v/v); $[\alpha]_D^{25}=-29.2°$ (c=1.00, CH$_3$OH). Anal. Calcd. for C$_{13}$H$_{21}$NO$_{10}$S$_2$: C, 37.59; H, 5.10; N, 3.37; S, 15.43 Found: C, 37.48; H, 5.06; N, 3.35; S, 15.38.

EXAMPLE 11

2,3-O-(1-Methylethylidene)-4,5-O-sulfonyl-β-D-fructopyranose Cyclooctylsulfamate Excess anhydrous cyclooctylamine (3.01 g, 0.0236 mol) was reacted with 2,3-O-(1-methylethylidene)-4,5-O-sulfonyl-β-D-fructopyranose chlorosulfate (3.00 g, 0.0079 mol) in the same manner as described in Example 4 to give 2.10 g (57%) of 2,3-O-(1-methylethylidene)-4,5-O-sulfonyl-β-D-fructopyranose cyclooctylsulfamate as a white foam after chromatography on silica gel eluting with hexane/EtOAc (7:3 v/v); $[\alpha]_D^{25}=-23.5°$ (c=1.00, CH$_3$OH). Anal. Calcd. for C$_{17}$H$_{29}$NO$_{10}$S$_2$: C, 43.40; H, 6.00; N, 2.98; S, 13.63. Found: C, 43.40; H, 6.13; N, 3.01; S, 13.72.

EXAMPLE 12

2,3-O-(1-Methylethylidene)-4,5-O-sulfonyl-β-D-fructopyranose (2,2,2-Trifluoroethyl)sulfamate Excess anhydrous 2,2,2-trifluoroethylamine (3.12 g, 0.0315 mol) was reacted with 2,3-O-(1-methylethylidene)-4,5-O-sulfonyl-β-D-fructopyranose chlorosulfate (2.00 g, 0.0053 mol) in the same manner as described for Example 4 to give 1.83 g (79%) of 2,3-O-(1-methylethylidene)-4,5-O-sulfonyl-β-D-fructopyranose (2,2,2-trifluoroethyl)sulfamate as a clear crystalline solid after chromatography on silica gel eluting with hexane/EtOAc (7:3 v/v); mp 125–127° C.; $[\alpha]_D^{25}=-24.3°$ (c=1.00, CH$_3$OH). Anal. Calcd. for C$_{11}$H$_{16}$F$_3$NO$_{10}$S$_2$: C, 29.80; H, 3.64; N, 3.16; S, 14.40. Found: C, 30.04; H, 3.52; N, 3.10; S, 14.01.

EXAMPLE 13

2,3-O-(1-Methylethylidene)-4,5-O-sulfonyl-β-D-fructopyranose Dimethylsulfamate Sodium hydride (60% oil dispersion; 0.73 g, 0.0183 mol) was extracted three times with anhydrous Et$_2$O while under argon, suspended in 40 mL of dry THF and cooled to 5° C. 2,3-O-(1-Methylethylidene)-O-4,5-sulfonyl-β-D-fructopyranose sulfamate (i.e. Example 1; 3.00 g, 0.0083 mol) was added as a solid portion-wise at 5° C. over 10 min while stirring under argon. After the hydrogen evolution ceased, excess iodomethane (5.16 mL, 0.083 mol) was added. The reaction mixture was heated to reflux for 1 hour, concentrated in vacuo, acidified with ca. 20 mL of 1N HCl, diluted with saturated aqueous NaCl and extracted three times with EtOAc. The combined EtOAc extracts were extracted twice with aqueous 0.1N Na$_2$S$_2$O$_3$, twice with saturated aqueous NaHCO$_3$, twice with saturated aqueous NaCl, dried over anhydrous MgSO$_4$, filtered through Celite® and concentrated in vacuo to furnish 2.10 g of crude product. This material was recrystallized from 50 mL of EtOH/H$_2$O (2:3) to provide 1.78 g (55%) of 2,3-O-(1-methylethylidene)-4,5-O-sulfonyl-β-D-fructopyranose dimethylsulfamate; mp 109–111° C.; $[\alpha]_D^{25}=-25.3°$ (c=1.00, CH$_3$OH). Anal. Calcd. for C$_{11}$H$_{19}$NO$_{10}$S$_2$: C, 33.93; H, 4.92; N, 3.60; S, 16.47. Found: C, 34.20; H, 4.87; N, 3.55; S, 16.55.

EXAMPLE 14

2,3-O-(1-Methylethylidene)-4,5-O-sulfonyl-β-D-fructopyranose Diethylsulfamate Excess anhydrous N,N-diethylamine (1.73 g, 0.0236 mol) was reacted with 2,3-O-(1-methylethylidene)-4,5-O-sulfonyl-β-D-fructopyranose chlorosulfate (3.00 g, 0.0079 mol) in the same manner as described in Example 4 to give 1.55 g (47%) of 2,3-O-(1-methylethylidene)-4,5-O-sulfonyl-β-D-fructopyranose diethylsulfamate as a white foam after chromatography on silica gel eluting with hexane/EtOAc (7:3 v/v); $[\alpha]_{D25}=-26.3°$ (c=1.00, CH$_3$OH). Anal. Calcd. for C$_{13}$H$_{23}$NO$_{10}$S$_2$: C, 37.40; H, 5.55; N, 3.36; S, 15.36. Found: C, 37.39; H, 5.55; N, 3.33; S, 15.41.

EXAMPLE 15

2,3-O-(1-Methylethylidene)-4,5-O-sulfonyl-β-D-fructopyranose Azidosulfate

O-(1-Methylethylidene)-4,5-O-sulfonyl-β-D-fructopyranose chlorosulfate (2.00 g, 0.0053 mol), prepared as described in Example 3, was combined with anhydrous pyridine (0.83 g, 0.0105 mol) in 26 mL of anhydrous acetonitrile while stirring under argon. Sodium azide (0.68 g, 0.0105 mol) was added and the reaction mixture was stirred under argon at RT for 18 hours. The crude reaction mixture was filtered through Celite®, concentrated in vacuo, and purified by chromatography on silica gel eluting with hexane/EtOAc (4:1 v/v) to provide 1.76 g (87%) of 2,3-O-(1-methylethylidene)-4,5-O-sulfonyl-β-D-fructopyranose azidosulfate as a clear glass; $[\alpha]_D^{25}=-21.0°$ (c=1.00, $CH_3OH$). Anal. Calcd. for $CH_9H_{13}N_3O_{10}S_2$: C, 28.76; H, 3.58; N, 10.68; S, 16.30. Found: C, 28.77; H, 3.70; N, 10.29; S, 15.84.

EXAMPLE 16

(S)-2,3-O-(1-Methylethylidene)-4,5-O-sulfinyl-β-D-fructopyranose Sulfamate 2,3-O-(1-Methylethylidene)-1-O-phenylmethyl-β-D-fructopyranose (6.00 g, 0.0193 mol) was dissolved in 75 mL of anhydrous dioxane and heated to reflux while stirring under argon. Thionyl chloride (28 mL, 0.384 mol) was added dropwise over 10 min to the refluxing solution. After 15 min, the reaction mixture was cooled to RT and concentrated in vacuo. The residue was dissolved in EtOAc and extracted twice with saturated aqueous $NaHCO_3$, twice with saturated aqueous NaCl, dried over anhydrous $MgSO_4$, filtered through Celite®, and concentrated in vacuo to yield 6.50 g (95%) of a 2.1:1 diastereomeric mixture of the (S) and (R) isomers of 2,3-O-(1-methylethylidene)-1-O-phenylmethyl-4,5-O-sulfinyl-β-D-fructopyranose. The individual (S) and (R) diastereomers were isolated in isomerically pure form by chromatography on silica gel eluting with hexane/EtOAc (9:1 v/v). The fractions containing the faster eluting (S)-isomer were combined and concentrated in vacuo to give 4.05 g of (S)-2,3-O-(1-methylethylidene)-1-O-phenylmethyl-4,5-O-sulfinyl-β-D-fructopyranose as a white crystalline solid; mp 92–94° C. Similarly, the fractions containing the R-isomer were combined and concentrated in vacuo to give 1.93 g of (R)-2,3-O-(1-methylethylidene)-1-O-phenylmethyl-4,5-O-sulfinyl-β-D-fructopyranose as a clear oil.

The (S)-2,3-O-(1-methylethylidene)-1-O-phenylmethyl-4,5-O-sulfinyl-β-D-fructopyranose thus obtained (3.99 g, 0.112 mol) was dissolved in 560 mL of $CH_2Cl_2$ that had been previously saturated with water. N-Bromosuccinimide (1.99 g, 0.0112 mol) was added and the resulting solution was degassed with nitrogen over 60 min. The solution was cooled to 5° C. and the reaction was irradiated with a 150 watt incandescent flood light for 15 min, quenched with excess cyclohexene (7 mL) and basified with triethylamine (1.56 mL). The reaction was concentrated in vacuo, partially dissolved in 200 mL of EtOAc and filtered through Celite®. The filtrate was concentrated in vacuo and the residue was purified by column chromatography on silica gel eluting with hexane/$Et_2O$ (3:2 v/v) to give 2.43 g (81%) of (S)-2,3-O-(1-methylethylidene)-4,5-O-sulfinyl-β-D-fructopyranose as a clear oil.

The (S)-2,3-O-(1-methylethylidene)-4,5-O-sulfinyl-β-D-fructopyranose (2.29 g, 0.0086 mol) thus obtained and triethylamine (14 mL) were dissolved in anhydrous EtOAc (86 mL) and cooled to −60° C. while stirring under argon. Sulfamoyl chloride (6.45 g, 0.0558 mol) was added as a solid in one portion and the reaction was allowed to slowly warm to RT over 18 hr. The reaction was extracted twice with 3N HCl, twice with saturated aqueous $NaHCO_3$, twice with saturated NaCl, dried over anhydrous $MgSO_4$, filtered through Celite® and concentrated in vacuo to give 2.43 g of crude product as a tan solid. This material was recrystallized from 5 mL of anhydrous ethanol to provide 1.20 g (40%) of (S)-2,3-O-(1-methylethylidene)-4,5-O-sulfinyl-β-D-fructopyranose sulfamate as a white crystalline solid; mp 151.5–153.5° C.; $[\alpha]_D^{25}=-14.9°$ (c=1.00, $CH_3OH$). Anal. Calcd. for $C_9H_{15}NO_9S_2$: C, 31.30; H, 4.38; N, 4.06; S, 18.57. Found: C, 31.48; H, 4.39; N, 4.08; S, 18.46.

EXAMPLE 17

(R)-2,3-O-(1-Methylethylidene)-4,5-O-sulfinyl-β-D-fructopyranose Sulfamate

The (R)-2,3-O-(1-methylethylidene)-1-O-phenylmethyl-4,5-O-sulfinyl-β-D-fructopyranose (4.33 g, 0.0122 mol) that was prepared and isolated as described in Example 16 was oxidatively debenzylated with NBS (2.17 g, 0.0122 mol) in the same manner described for Example 16, i.e. the (S)-isomer, to provide 1.09 g (34%) of (R)-2,3-O-(1-methylethylidene)-4,5-O-sulfinyl-β-D-fructopyranose as a clear oil. Similarly, this material was reacted with sulfamoyl chloride (2.86 g, 0.0248 mol) and recrystallized from ethanol in the same manner described in Example 16 to furnish 0.25 g of (R)-2,3-O-(1-methylethylidene)-4,5-O-sulfinyl-β-D-fructopyranose sulfamate as a white crystalline solid; mp 197–199° C., decomp; $[\alpha]_D^{25}=-43.5°$ (c=1.00, $CH_3OH$). Anal. Calcd. for $C_9H_{15}NO_9S_2$: C, 31.30; H, 4.38; N, 4.06; S, 18.57. Found: C, 31.55; H, 4.41; N, 4.10; S, 18.33.

EXAMPLE 18

2,3-O-(1-Ethylpropylidene)-4,5-O-sulfonyl-β-D-fructopyranose Sulfamate

D-Fructose (100.0 g, 0.555 mol) was suspended in 3-pentanone (2.3 L, 1.127 mol) and heated to 40° C. and concd $H_2SO_4$ (60 mL) was added dropwise over 20 min. Twenty-five minutes after the addition, the reaction was cooled from 40° C. to 5° C., cautiously basified to pH 11 with 3N aqueous NaOH and concentrated in vacuo. The residue was diluted with water and extracted 3 times with $CH_2Cl_2$. The combined $CH_2Cl_2$ extracts were washed twice with water, dried over anhydrous $Na_2SO_4$, filtered through Celite® and concentrated in vacuo to give 18.5 g (11%) of product as a brown oil, which was purified by column chromatography on silica gel eluting with hexane/EtOAc (6:1 v/v) to give 2,3:4,5-bis-O-(1-ethylpropylidene)-β-D-fructopyranose as a white crystalline solid; mp 46-48° C.; $[\alpha]_D^{25}=-36.6°$ (c=1.00, $CH_3OH$). Anal. Calcd. for $C_{16}H_{28}O_6$: C, 60.74; H, 8.92. Found: C, 60.77; H, 8.93.

2,3:4,5-Bis-O-(1-Ethylpropylidene)-β-D-fructopyranose (17.19 g, 0.0541 mol) was combined with pyridine (5.13 g, 0.0649 mol) and dissolved in 73 mL of dry toluene. This solution was added dropwise over 15 min at −20° C. to a vigorously stirred solution of sulfuryl chloride (8.75 g, 0.0649 mol) in 75 mL of dry toluene. After the addition, the reaction was allowed to slowly warm to RT over 3 hr, and diluted with water. The toluene layer was extracted 3 times with 10% aqueous citric acid, three times with saturated aqueous $NaHCO_3$, twice with saturated aqueous NaCl, dried over anhydrous $Na_2SO_4$, filtered through Celite® and concentrated in vacuo to afford 25.4 g of crude 2,3:4,5-bis-O-(1-ethylpropylidene)-β-D-fructopyranose chlorosulfate. This crude chlorosulfate was dissolved in dry THF (300 mL) and placed in a vigorously stirred autoclave under 30 psig of anhydrous ammonia over 18 hr. The reaction was filtered through Celite® and concentrated in vacuo. The residue was purified by column chromatography on silica gel eluting with hexane/EtOAc (3:1 v/v) to give 2,3:4,5-bis-O-(1-ethylpropylidene)-β-D-fructopyranose sulfamate as a clear syrup; $[\alpha]_D^{25}=-19.7°$ (c=1.00, $CH_3OH$). Anal. Calcd. for $C_{16}H_{29}NO_8S$: C, 48.59; H, 7.39; N, 3.54; S, 8.11. Found: C, 48.36; H, 7.41; N, 3.51; S, 8.11.

2,3:4,5-Bis-O-(1-Ethylpropylidene)-β-D-fructopyranose sulfamate (14.56 g, 0.0368 mol) was dissolved in THF (362 mL), heated to 43° C. and acidified with 184 mL of 6N aqueous HCl while stirring vigorously. After 1 hr, the reaction was cooled to 5° C., the pH was adjusted to pH 7 with $Na_2CO_3$ and the aqueous layer was saturated with NaCl. The resulting layers were separated and the aqueous layer was extracted 2 more times with THF. The combined THF extracts were dried over anhydrous $MgSO_4$, filtered through Celite® and concentrated in vacuo. The residue was purified by column chromatography on silica gel eluting with $EtOAc/CH_2Cl_2$ (3:2 v/v) to give 2.53 g (21%) of 2,3-O-(1-ethylpropylidene)-β-D-fructopyranose 1-sulfamate as a clear syrup; $[\alpha]_D^{25}=+22.7°$ (c=1.00, $CH_3OH$). Anal. Calcd. for $C_{11}H_{21}NO_8S$: C, 40.36; H, 6.47; N, 4.28; S, 9.79. Found: C, 40.46; H, 6.50; N, 4.12; S, 9.66.

2,3-O-(1-Ethylpropylidene)-β-D-fructopyranose 1-sulfamate (1.82 g, 0.0056 mol) and pyridine (1.06 mL, 0.0134 mol) were dissolved in EtOAc (55 mL) and reacted with sulfuryl chloride (1.65 g, 0.0122 mol) as described for Example 1 to provide the corresponding bis-chlorosulfate. Analogous dechlorosulfation of this bis-chlorosulfate with $NaHCO_3$ (2.67 g, 0.0318 mol) in methanol (16 mL) followed by purification by preparative TLC on silica gel eluting with $Et_2O$/hexane (7:3 v/v) provided 0.79 g of 2,3-O-(1-ethylpropylidene)-4,5-O-sulfonyl-β-D-fructopyranose sulfamate as a white crystalline solid; mp 130–133° C.; $[\alpha]_D^{25}=-3.1°$ (c=1.17, $CH_3OH$). Anal. Calcd. for $C_{11}H_{19}NO_{10}S_2$: C, 33.93; H, 4.92; N, 3.60; S, 16.47. Found: C, 34.21; H, 4.95; N, 3.54; S, 16.29.

EXAMPLE 19

2,3-O-(1-Methylethylidene)-4,5-O-[N-(4-methylbenzenesulfonyl)imidosulfinyl]-β-D-fructopyranose Sulfamate To a solution of 2,3-O-(1-methylethylidene)-β-D-fructopyranose 1-sulfamate (10.0 g, 0.0334 mol) in 120 mL of dry THF was added a solution of crude N-(p-toluenesulfonyl)imidothionyl chloride (34.1 g, 0.1254 mol) in 120 mL of dry benzene dropwise at 5° C. over 15 min while stirring vigorously under argon. The reaction was allowed to slowly warm to RT over 2 hr and was subsequently concentrated in vacuo. The residue was cautiously quenched with saturated aqueous $NaHCO_3$ and extracted with EtOAc. The basic aqueous layer was extracted two more times with EtOAc, and the combined EtOAc extracts were extracted with saturated aqueous $NaHCO_3$, twice with saturated aqueous NaCl, dried over anhydrous $MgSO_4$, filtered through Celite® and concentrated in vacuo. The residue was dissolved in 200 mL of boiling $CH_2Cl_2$/EtOAc (19:1 v/v) and p-toluenesulfonamide precipitated from the solution on cooling to RT. The p-toluenesulfonamide was isolated by filtration and the filtrate was purified by column chromatography on silica gel eluting with $CH_2Cl_2$/EtOAc (19:1 v/v) to give 9.35 g (56%) of 2,3-O-(1-methylethylidene)-4,5-O-[N-(4-methylbenzenesulfonyl) imido-sulfinyl]-β-D-fructopyranose sulfamate as a white foam; mp 68–73° C.; $[\alpha]_D^{25}=+23.3°$ (c=1.00, $CH_3OH$). Anal. Calcd. for $C_{16}H_{22}N_2O_{10}S_3$: C, 38.55; H, 4.45; N, 5.64; S, 19.29. Found: C, 38.52; H, 4.57; N, 5.38; S, 19.07.

EXAMPLE 20

2,3-O-(1-Methylethylidene)-4,5-O-[N-(4-methylbenzenesulfonyl)imido-sulfonyl]-β-D-fructo pyranose Sulfamate 2,3-O-(1-Methylethylidene)-4,5-O-[N-(4-methylbenzenesulfonyl) imidosulfinyl]-β-D-fructopyranose sulfamate (3.10 g, 0.0062 mol) was dissolved in 19 mL of $CH_3CN$ and diluted with 19 mL of $CCl_4$. Water (28 mL) was added and this mixture was cooled to 5° C. while stirring vigorously with a mechanical stirrer. Sodium periodate (2.92 g, 0.0136 mol) was added followed by a catalytic amount of $RuCl_3.H_2O$ (0.0300 g, 0.00015 mol). The reaction was allowed to warm to RT over 20 hr and diluted with 150 mL of EtOAc. The layers were separated and the aqueous layer was extracted two more times with EtOAc. The combined EtOAc extracts were washed twice with saturated aqueous NaCl, dried over anhydrous $MgSO_4$, filtered through Celite® and concentrated in vacuo. The residue was purified by column chromatography on silica gel eluting with $Et_2O$/hexane (4:1 v/v), dissolved in $CH_2Cl_2$, filtered through Celite® and concentrated in vacuo to give 0.72 g (23%) of 2,3-O-(1-methylethylidene)-4,5-O-[N-(4-methylbenzenesulfonyl)imidosulfonyl]-β-D-fructopyranose sulfamate as a solvate with $CH_2Cl_2$ and n-hexane that appears as a hard white foam; mp 77–101° C.; $[\alpha]_D^{25}=+4.1°$ (c=1.00, $CH_3OH$). Anal. Calcd. for $C_{16}H_{22}N_2O_{11}S_3.0.2$ $CH_2Cl_2.0.1$ $C_6H_{14}$: C, 37.32; H, 4.43; N, 5.20; S, 17.86. Found: C, 37.64; H, 4.48; N, 5.11; S, 17.76.

EXAMPLE 21

2,3-O-(Cyclohexylidene)-4,5-O-sulfonyl-δ-D-fructopyranose Sulfamate 2,3:4,5-Bis-O-(Cyclohexylidene)-β-D-fructopyranose (22.6 g, 0.0664 mol; U.S. Pat. No. 4,659,809) was combined with pyridine (6.30 g, 0.0797 mol) and dissolved in 150 mL of dry toluene. This solution was added dropwise over 20 min at −20° C. to a vigorously stirred solution of sulfuryl chloride (8.75 g, 0.0649 mol) in 150 mL of dry toluene. After the addition, the reaction was allowed to slowly warm to RT over 4 hr, and diluted with water. The toluene layer was extracted 3 times with 10% aqueous citric acid, three times with saturated aqueous $NaHCO_3$, twice with saturated aqueous NaCl, dried over anhydrous $MgSO_4$, filtered through Celite® and concentrated in vacuo to afford 33.1 g of crude 2,3:4,5-bis-O-(cyclohexylidene)-β-D-fructopyranose chlorosulfate. This crude chlorosulfate was dissolved in 132 mL of dry THF and placed in a vigorously stirred autoclave under 30 psig of anhydrous ammonia over 18 hr. The reaction was filtered through Celite® and concentrated in vacuo. The residue was purified by column chromatography on silica gel eluting with hexane/EtOAc (7:3 v/v) to give 2,3:4,5-bis-O-(cyclohexylidene)-β-D-fructopyranose sulfamate as a hard white foam; $[\alpha]_D^{25}=-31.7°$ (c=1.00, $CH_3OH$). Anal. Calcd. for $C_{18}H_{29}NO_8S.0.14$ EtOAc: C, 51.62; H, 7.03; N, 3.24; S, 7.42. Found: C, 51.58; H, 7.02; N, 3.30; S, 7.70.

2,3:4,5-Bis-O-(Cyclohexylidene)-β-D-fructopyranose sulfamate (20.37 g, 0.0486 mol) was dissolved in THF (408 mL), acidified with 204 mL of 6N aqueous HCl and heated at 47–50° C. for 5 hr while stirring vigorously. The reaction was cooled to 5° C., the pH was cautiously adjusted to pH 7 with $Na_2CO_3$ and the aqueous layer was saturated with NaCl. The resulting layers were separated and the aqueous layer was extracted 3 more times with THF. The combined THF extracts were dried over anhydrous $MgSO_4$, filtered through Celite® and concentrated in vacuo. The residue was purified by column chromatography on silica gel eluting with $EtOAc/CH_2Cl_2$ (3:2 v/v) to give 2.85 g (17%) of 2,3-O-(cyclohexylidene)-β-D-fructopyranose 1-sulfamate as a white foam.

2,3-O-(Cyclohexylidene)-β-D-fructopyranose 1-sulfamate (2.33 g, 0.0069 mol) was combined with pyridine (1.22 mL, 0.0151 mol), dissolved in EtOAc (69 mL) and reacted with sulfuryl chloride (1.33 mL, 0.0165 mol) in the same manner as described for Example 1 to provide the corresponding bis-chlorosulfate. Analogous dechlorosulfation of this bis-chlorosulfate with $NaHCO_3$ (3.76 g, 0.0448 mol) in methanol (69 mL) followed by purification by column chromatography on silica gel with hexane/EtOAc (7:3 v/v) provided 1.42 g of product, which was recrystallized from 20 mL of $EtOH/H_2O$ (1:1 v/v) to provide 1.21 g (44%) of 2,3-O-(cyclohexylidene)-4,5-O-sulfonyl-β-D-fructopyranose sulfamate as a white crystalline solid; mp 139–141° C.; $[\alpha]_D^{25}=-31.5°$ (c=1.00, $CH_3OH$). Anal. Calcd. for $C_{12}H_{19}NO_{10}S_2$: C, 35.91; H, 4.77; N, 3.49; S, 15.97. Found: C, 36.08; H, 4.81; N, 3.45; S, 15.87.

EXAMPLE 22

(S)-4,5-O-[N-(1,1-Dimethylethoxycarbonyl) imidosulfinyl]-2,3-O-(1-methyl-ethylidene)-β-D-fructopyranose Sulfamate N,N-Dichloro-t-butylcarbamate (10.0 g, 0.0537 mol) was combined with sulfur (1.72 g, 0.0537 mol) and tetrabutylammonium bromide (1.73 g, 0.0054 mol) in 50 mL of anhydrous benzene. The resulting suspension was heated at 40° C. for 2 hr while stirring vigorously under argon. After cooling to RT, the resulting solution of crude N-(t-butoxycarbonyl)imidothionyl chloride was transferred, while under argon, to an addition funnel and added dropwise at 5° C. over 15 min to a vigorously stirred solution of 2,3-O-(1-methylethylidene)-β-D-fructopyranose 1-sulfamate (5.19 g, 0.0173 mol) and anhydrous pyridine (4.60 mL, 0.0568 mol) in 173 mL of anhydrous THF. The reaction was stirred at 5° C. for 3 hr, filtered through Celite® and concentrated in vacuo. The crude residue was dissolved in EtOAc and extracted twice with saturated aqueous $NaHCO_3$, twice with saturated aqueous NaCl, dried over anhydrous $MgSO_4$, filtered through Celite® and concentrated in vacuo. The residue was purified by column chromatography on silica gel eluting with hexane/EtOAc (7:3 v/v) and recrystallized from 25 mL of anhydrous ethanol to yield 2.11 g (27%) of (S)-4,5-O-[N-(1,1dimethylethoxycarbonyl)imidosulfinyl]-2,3-O-(1-methylethylidene)-β-D-fructopyranose sulfamate as a white crystalline solid; mp 175–176° C.; $[\alpha]_D^{25}=+19.5°$ (c=1.00, $CH_3OH$). Anal. Calcd. for $C_{14}H_{24}N_2O_{10}S_2$: C, 37.83; H, 5.44; N, 6.30; S, 14.43. Found: C, 38.05; H, 5.45; N, 6.36; S, 14.36.

What is claimed is:

1. A method for treating ischemia-induced neurodegeneration comprising administering to a mammal afflicted with such condition a therapeutically effective amount of a compound of the formula I:

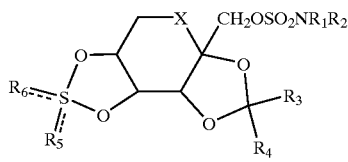

wherein

X is methylene or oxygen;

$R_1$ and $R_2$ are the same or different and chosen from hydrogen, $C_1–C_6$ alkyl, $C_3–C_6$ cycloalkyl, benzyl, allyl, or $C_1–C_6$ perfluoroalkylmethyl, or taken together as $N_2$ to define an azide group;

$R_3$ and $R_4$ are the same or different and chosen from hydrogen or $C_1–C_6$ alkyl;

$R_5$ and $R_6$ may be the same or different and are selected from oxygen, a lone pair of electrons or $NR_7$; wherein $R_7$ is selected from hydrogen, $C_1–C_6$ alkyl, $C_1–C_6$ perfluoroalkyl, arenesulfonyl, $C_1–C_6$ alkoxycarbonyl or arenemethyloxycarbonyl and the pharmaceutically acceptable salts thereof.

2. A method for the prevention or treatment of acute ischemia-induced neurodegeneration in a mammal which comprises administering to the mammal a therapeutically effective amount of the compound of formula (I) as recited in claim 1.

3. A method for the prevention or treatment of acute ischemia-induced neurodegeneration of claim 2 wherein said neurodegeneration as occurs during and after stroke.

4. A method for the prevention or treatment of acute ischemia-induced neurodegeneration of claim 2 wherein said neurodegeneration as occurs during and after head trauma.

5. A method for the prevention or treatment of acute ischemia-induced neurodegeneration of claim 2 wherein said neurodegeneration as occurs during and after spinal injury.

6. A method for the prevention or treatment of acute ischemia-induced neurodegeneration of claim 2 wherein said neurodegeneration as occurs during and after non-fatal cardiac arrest.

7. The method for the prevention or treatment of acute ischemia-induced neurodegeneration of claim 2 wherein said neurodegeneration as occurs during and after major surgical procedures.

8. The method of claim 1, wherein the therapeutically effective amount is from about 400 to 2000 mg.

9. The method of claim 1, wherein the amount is from about 1 to 400 mg.

10. The method of claim 1, wherein said compound is in the β-D-fructopyranose or pseudo-β-D-fructopyranose absolute configuration.

11. The method of claim 1, wherein said compound is in the β-L-fructopyranose or pseudo-β-L-fructopyranose absolute configuration.

12. The method of claim 1, wherein in the compound of formula I $R_5$ and $R_6$ are oxygen.

13. The method of claim 1, wherein in the compound of formula I $R_5$ is oxygen and $R_6$ is a lone pair of electrons.

14. The method of claim 1, wherein in the compound of formula I $R_5$ is a lone pair of electrons and $R_6$ oxygen.

15. The method of claim 1, wherein in the compound of formula I $R_1$ and $R_2$ are hydrogen.

16. The method of claim 1, wherein in the compound of formula I $R_1$ is hydrogen.

17. The method of claim 1, wherein in the compound of formula I $R_3$ and $R_4$ are methyl.

18. The method of claim 1, wherein in the compound of formula I $R_1$ is hydrogen, and $R_2$ is methyl, cyclopropyl or cyclobutyl.

19. The method of claim 1, wherein in the compound of formula I X is oxygen or methylene, $R_1$ and $R_2$ are hydrogen or methyl, $R_3$ and $R_4$ are methyl, $R_5$ and $R_6$ are oxygen.

20. The method of claim 1, wherein said compound of formula I is selected from the group consisting of:

2,3-O-(1-methylethylidene)-4,5-O-sulfonyl-β-D-fructopyranose sulfamate,
2,3-O-(1-methylethylidene)-4,5-O-sulfonyl-β-L-fructopyranose sulfamate,
2,3-O-(1-methylethylidene)-4,5-O-sulfonyl-β-D-fructopyranose methylsulfamate,
2,3-O-(1-methylethylidene)-4,5-O-sulfonyl-β-D-fructopyranose butylsulfamate,
2,3-O-(1-methylethylidene)-4,5-O-sulfonyl-β-D-fructopyranose ethylsulfamate,
2,3-O-(1-methylethylidene)-4,5-O-sulfonyl-β-D-fructopyranose octylsulfamate,
2,3-O-(1-methylethylidene)-4,5-O-sulfonyl-β-D-fructopyranose 2-propenylsulfamate,
2,3-O-(1-methylethylidene)-4,5-O-sulfonyl-β-D-fructopyranose phenylmethylsulfamate,
2,3-O-(1-methylethylidene)-4,5-O-sulfonyl-β-D-fructopyranose cyclopropylsulfamate,
2,3-O-(1-methylethylidene)-4,5-O-sulfonyl-β-D-fructopyranose cyclobutylsulfamate,
2,3-O-(1-methylethylidene)-4,5-O-sulfonyl-β-D-fructopyranose cyclooctylsulfamate,
2,3-O-(1-methylethylidene)-4,5-O-sulfonyl-β-D-fructopyranose (2,2,2-trifluoroethyl)-sulfamate,
2,3-O-(1-methylethylidene)-4,5-O-sulfonyl-β-D-fructopyranose dimethylsulfamate,
2,3-O-(1-methylethylidene)-4,5-O-sulfonyl-β-D-fructopyranose diethylsulfamate,
2,3-O-(1-methylethylidene)-4,5-O-sulfonyl-β-D-fructopyranose azidosulfate,
(S)-2,3-O-(1-methylethylidene)-4,5-O-sulfinyl-β-D-fructopyranose sulfamate,
(R)-2,3-O-(1-methylethylidene)-4,5-O-sulfinyl-β-D-fructopyranose sulfamate,
2,3-O-(1-ethylpropylidene)-4,5-O-sulfonyl-β-D-fructopyranose sulfamate,
2,3-O-(1-methylethylidene)-4,5-O-[N-(4-methylbenzenesulfonyl)imidosulfinyl]-β-D-fructopyranose sulfamate,
2,3-O-(1-methylethylidene)-4,5-O-[N-(4-methylbenzenesulfonyl)imidosulfonyl]-β-D-fructopyranose sulfamate,
2,3-O-(cyclohexylidene)-4,5-O-sulfonyl-β-D-fructopyranose sulfamate,
(R)-4,5-O-[N-(1,1-dimethylethoxycarbonyl)imidosulfinyl]-2,3-O-(1-methylethylidene)-β-D-fructopyranose sulfamate,
(S)-4,5-O-[N-(1,1-dimethylethoxycarbonyl)imidosulfinyl]-2,3-O-(1-methylethylidene)-β-D-fructopyranose sulfamate, and the pharmaceutically acceptable salts thereof.

21. The method of claim 1, wherein said compound of formula I is selected from the group consisting of:

2,3-O-(1-methylethylidene)-4,5-O-sulfonyl-pseudo-β-D-fructopyranose sulfamate,
2,3-O-(1-methylethylidene)-4,5-O-sulfonyl-pseudo-β-L-fructopyranose sulfamate,
2,3-O-(1-methylethylidene)-4,5-O-sulfonyl-pseudo-β-D-fructopyranose methylsulfamate,
2,3-O-(1-methylethylidene)-4,5-O-sulfonyl-pseudo-β-D-fructopyranose cyclopropyl-sulfamate,
2,3-O-(1-methylethylidene)-4,5-O-sulfonyl-pseudo-β-D-fructopyranose cyclobutyl-sulfamate,
(S)-2,3-O-(1-methylethylidene)-4,5-O-sulfinyl-pseudo-β-D-fructopyranose sulfamate,
(R)-2,3-O-(1-methylethylidene)-4,5-O-sulfinyl-pseudo-β-D-fructopyranose sulfamate, and the pharmaceutically acceptable salts thereof.

22. The method of claim 20 wherein said compound is 2,3-O-(1-methylethylidene)-4,5-O-sulfonyl-β-D-fructopyranose sulfamate, and the pharmaceutically acceptable salts thereof.

23. The method of claim 21 wherein said compound is 2,3-O-(1-methylethylidene)-4,5-O-sulfonyl-pseudo-β-D-fructopyranose sulfamate, and the pharmaceutically acceptable salts thereof.

24. A pharmaceutical composition effective for the treatment or prevention of acute ischemia-induced neurodegeneration comprising an amount of a compound of formula I as recited in claim 1 in admixture with a pharmaceutically acceptable carrier.

25. The pharmaceutical composition of claim 24, wherein said compound of formula I is present in a unit dosage amount of about 2.5 milligrams to about 1000 milligrams.

* * * * *